(12) United States Patent
Nishikawa et al.

(10) Patent No.: US 7,235,399 B2
(45) Date of Patent: Jun. 26, 2007

(54) METHOD FOR PRODUCING OPTICALLY ACTIVE 3-CHLORO-2-METHYL-1, 2-PROPANEDIOL TAKING ADVANTAGE OF MICROORGANISM

(75) Inventors: Kouji Nishikawa, Osaka (JP); Toshio Suzuki, Osaka (JP); Atsushi Nakagawa, Osaka (JP); Keiko Suzuki, Osaka (JP); Satoshi Nakayama, Osaka (JP)

(73) Assignee: Daiso Co., Ltd., Osaka (JP)

( * ) Notice: Subject to any disclaimer, the term of this patent is extended or adjusted under 35 U.S.C. 154(b) by 168 days.

(21) Appl. No.: 11/028,933

(22) Filed: Jan. 4, 2005

(65) Prior Publication Data

US 2005/0153409 A1   Jul. 14, 2005

(30) Foreign Application Priority Data

Jan. 5, 2004   (JP)   ............................. 2004-000298

(51) Int. Cl.
*C12P 41/00*   (2006.01)

(52) U.S. Cl. .................................................. 435/280

(58) Field of Classification Search ............... None
See application file for complete search history.

(56) References Cited

U.S. PATENT DOCUMENTS

2006/0019359 A1   1/2006   Suzuki et al.

FOREIGN PATENT DOCUMENTS

| EP | 0 435 551 | 7/1991 |
|---|---|---|
| EP | 0 745 681 | 12/1996 |
| EP | 1 096 019 | 5/2001 |
| JP | 63-251098 | 10/1988 |
| JP | 01-51999 | 11/1989 |
| JP | 03-191794 | 8/1991 |
| JP | 03-191795 | 8/1991 |
| JP | 06-30790 | 2/1994 |
| JP | 1994-30790 | 2/1994 |
| JP | 06-209781 | 8/1994 |
| JP | 1994-209781 | 8/1994 |
| JP | 2001-120296 | 5/2001 |
| JP | 2001-149090 | 6/2001 |
| JP | 2002-253295 | 9/2002 |

OTHER PUBLICATIONS

Kasai et al., *Industrialization of the Microbial Resolution of Chiral $C_3$ and $C_4$ Synthetic Units: From a Small Beginning to a Major Operation*, a Personal Account, Advanced Synthesis & Catalysis, 345, No. 4, pp. 437-455, 2003.

*Primary Examiner*—Sandra E. Saucier
(74) *Attorney, Agent, or Firm*—Westerman, Hattori, Daniels & Adrian, LLP.

(57) ABSTRACT

The present invention provides a method for obtaining optically active 3-chloro-2-methyl-1,2-propanediol, the method comprising: a first step of letting at least one kind of microorganism or processed product thereof having an ability to leave untouched (R)-3-chloro-2-methyl-1,2-propanediol or (S)-3-chloro-2-methyl-1,2-propanediol in the presence of an enantiomeric 3-chloro-2-methyl-1,2-propanediol mixture act on an enantiomeric 3-chloro-2-methyl-1,2-propanediol mixture; and a second step of recovering the untouched optically active 3-chloro-2-methyl-1,2-propanediol.

14 Claims, No Drawings

US 7,235,399 B2

METHOD FOR PRODUCING OPTICALLY ACTIVE 3-CHLORO-2-METHYL-1, 2-PROPANEDIOL TAKING ADVANTAGE OF MICROORGANISM

BACKGROUND OF THE INVENTION

1. Field of the Invention

The present invention relates to a method for obtaining an optically active isomer of 3-chloro-2-methyl-1,2-propanediol from an enantiomeric mixture of 3-chloro-2-methyl-1,2-propanediol by taking advantage of a microorganism.

2. Description of the Related Art

Optically active isomers of 3-chloro-2-methyl-1,2-propanediol are very important and useful compounds in the production of pharmaceuticals, agrichemicals, physiologically active substances, and like optically active compounds. For example, a tertiary methyl carbinol derivative obtained from (S)-3-chloro-2-methyl-1,2-propanediol according to the method disclosed in Japanese Patent No. 2567430 is for use as a production intermediate for d-α-tocopherol (natural vitamin E). A hydroquinone derivative obtained from (R)-3-chloro-2-methyl-1,2-propanediol according to the method disclosed in Japanese Patent No. 2557068 is of use as a production intermediate for d-α-tocopherol.

Therefore, a method for efficiently obtaining optically active 3-chloro-2-methyl-1,2-propanediol is required.

Examples of methods for obtaining optically active 1,2-diol are:

(1) letting a microorganism act on a racemic 3-halogeno-1,2-propanediol to give an optically active 3-halogeno-1,2-propanediol (Japanese Unexamined Patent Publication Nos. 1988-251098 and 1994-209781);
(2) letting a microorganism act on racemic 1,2-propanediol to give optically active 1,2-propanediol (Japanese Unexamined Patent Publication No. 1994-30709); and
(3) use of a cobalt salen catalyst to give optically active 1,2-propanediol (*Science* 1997, 277, 936-938). These publications, however, are silent as to optically active 3-chloro-2-methyl-1,2-propanediol.

A known method for producing an optically active 3-chloro-2-methyl-1,2-propanediol isomer is by a chemical synthesis using an optically active tartaric acid ester (Japanese Patent No. 2567430). The method disclosed therein requires expensive ingredients and a low-temperature (−18° C.) reaction and takes a long period of time to complete, therefore being impractical. In comparison, a reaction using a microorganism could presumably be carried out under mild conditions without expensive ingredients.

As examples of microorganisms that can produce optically active alcohols, *Pseudomonas* sp. DS-K-436-1 is described as having an ability to stereoselectively dehalogenate (R)-4-halogeno-1,3-butanediol in Japanese Unexamined Patent Publication No. 2001-120296, and *Pseudomonas* sp. OS-K-29 is described as having an ability to assimilate (R)-2,3-dibromo-1-propanol in Japanese Examined Patent Publication No. 1989-51999. Moreover, *Pseudomonas* sp. DS-SI-5, *Pseudomonas nitroreducens* DS-S-RP8 and *Alcaligenes* sp. DS-S-7G are described as having an ability to assimilate (R)-3-halogeno-1,2-propanediol or (S)-1,2-propanediol in Japanese Unexamined Patent Publication Nos. 1991-191795, 2001-149090 and 2002-253295.

However, the microorganisms disclosed in Japanese Unexamined Patent Publication Nos. 2001-120296, 1991-191795, 2001-149090 and 2002-253295 and Japanese Examined Patent Publication No. 1989-51999 are described as usable in the production of just optically active secondary alcohols. These publications do not discuss the production of a tertiary alcohol, e.g., 3-chloro-2-methyl-1,2-propanediol, using the aforementioned microorganisms.

In Japanese Unexamined Patent Publication No. 1991-191794, *Pseudomonas* sp. DS-K-2D1 is described as having an ability to assimilate a secondary alcohol, i.e., a (S)-3-halogeno-1,2-propanediol, while sustaining the (R)-3-halogeno-1,2-propanediol. However, this microorganism does not have an ability to sustain an optically active isomer of 3-chloro-2-methyl-1,2-propanediol within an enantiomeric mixture of a tertiary alcohol, i.e., 3-chloro-2-methyl-1,2-propanediol.

As described above, microorganisms that can stereoselectively resolve secondary alcohols do not necessarily have an ability to stereoselectively resolve tertiary alcohols.

A practical method for inexpensively obtaining optically active 3-chloro-2-methyl-1,2-propanediol in large amounts has been heretofore unknown.

BRIEF SUMMARY OF THE INVENTION

An object of the invention is to provide a method for readily obtaining optically active 3-chloro-2-methyl-1,2-propanediol with high optical purity.

The inventors conducted extensive research to achieve the object described above, and found that:

(i) specific microorganisms have an ability to stereoselectively resolve 3-chloro-2-methyl-1,2-propanediol or an ability to leave untouched an optically active 3-chloro-2-methyl-1,2-propanediol isomer when acting on an enantiomeric 3-chloro-2-methyl-1,2-propanediol mixture;
(ii) the aforementioned stereoselective resolution by such microorganisms can be enhanced by conducting it under aerobic conditions; and
(iii) an enantiomeric 3-chloro-2-methyl-1,2-propanediol mixture can be readily synthesized chemically by, for example, a ring-opening reaction hydrolysis of 2-methyl-epichlorohydrin existing sulfuric acid as a catalyst.

The present invention has been accomplished based on the findings described above and provides methods for obtaining optically active 3-chloro-2-methyl-1,2-propanediol:

1. A method for obtaining optically active 3-chloro-2-methyl-1,2-propanediol, the method comprising:

a first step of letting at least one kind of microorganism or processed product thereof having an ability to leave untouched (R)-3-chloro-2-methyl-1,2-propanediol or (S)-3-chloro-2-methyl-1,2-propanediol in the presence of an enantiomeric 3-chloro-2-methyl-1,2-propanediol mixture act on an enantiomeric 3-chloro-2-methyl-1,2-propanediol mixture; and a second step of recovering the untouched optically active 3-chloro-2-methyl-1,2-propanediol.

2. A method according to Item 1, wherein the microorganism is at least one kind of microorganism belonging to the genus *Pseudomonas* and having an ability to leave untouched (R)-3-chloro-2-methyl-1,2-propanediol in the presence of an enantiomeric 3-chloro-2-methyl-1,2-propanediol mixture, and the optically active 3-chloro-2-methyl-1,2-propanediol obtained is (R)-3-chloro-2-methyl-1,2-propanediol.

3. A method according to Item 2, wherein the microorganism belonging to the genus *Pseudomonas* is at least one kind of microorganism selected from the group consisting of *Pseudomonas* sp. DS-K-436-1 (International Deposition No: FERM BP-7079) and *Pseudomonas* sp. OS-K-29 (International Deposition No: FERM BP-994).

4. A method according to Item 1, wherein the microorganism is at least one kind of microorganism that is selected from the group consisting of microorganisms belonging to the genus *Pseudomonas* and microorganisms belonging to the genus *Alcaligenes* and that has an ability to leave untouched (S)-3-chloro-2-methyl-1,2-propanediol in the presence of an enantiomeric 3-chloro-2-methyl-1,2-propanediol mixture, and the optically active 3-chloro-2-methyl-1,2-propanediol obtained is (S)-3-chloro-2-methyl-1,2-propanediol.

5. A method according to Item 4, wherein the microorganism is at least one kind of microorganism selected from the group consisting of *Pseudomonas* sp. DS-SI-5 (International Deposition No: FERM BP-7080), *Pseudomonas nitroreducens* DS-S-RP8 (International Deposition No: BP-7793), and *Alcaligenes* sp. DS-S-7G (International Deposition No: FERM BP-3098).

6. A method according to Item 1, wherein the first step is carried out under aerobic conditions.

7. A method according to Item 1, wherein in the first step, the pH of the reaction system is 4 to 6.5.

8. A method according to Item 1, wherein the enantiomeric 3-chloro-2-methyl-1,2-propanediol mixture is obtained by ring-opening hydrolyzing an enantiomeric 2-methyl-epichlorohydrin mixture under acidic conditions created by sulfuric acid.

According to the present invention, optically active 3-chloro-2-methyl-1,2-propanediol with high optical purity can be obtained from an enantiomeric 3-chloro-2-methyl-1,2-propanediol mixture using microorganisms. Due to the stereoselective resolution by the microorganisms, the method of the invention is simple, does not require expensive ingredients or reagents, and can be carried out under mild conditions. Therefore, the method of the invention is industrially highly advantageous.

*Pseudomonas* sp. DS-K-436-1, International Deposition No. FERM BP-7079, was deposited at the National Institute of Bio-Science and Human-Technology, Agency of Industrial Science and Technology, 1-3, Higashi 1-chome, Tsukuba-shi, Ibaraki-ken, 305-8566 Japan, on October 7, 1999, and accepted as established under the Budapest Treaty on the International Recognition of the Deposit of Microorganisms for the Purposes of Patent Procedure.

*Pseudomonas* sp. OS-K-29, International Deposition No. FERM BP-994, was deposited at the Fermentation Research Institute, Agency of Industrial Science and Technology, 1-3, Higashi 1-chome, Yatabe-machi. Tsukuba-gun, Ibaraki-ken, 305 Japan, on Sep. 14, 1984, and accepted as established under the Budapest Treaty on the International Recognition of the Deposit of Microorganisms for the Purposes of Patent Procedure. *Pseudomonas* sp. DS-SI-5, International Deposition No. FERM BP-7080, was deposited at the National Institute of Bio-Science and Human-Technology, Agency of Industrial Science and Technology, 1-3, Higashi 1-chome. Tsukuba-shi, Ibaraki-ken. 305-8566 Japan, on Oct. 7, 1999. and accepted as established under the Budapest Treaty on the International Recognition of the Deposit of Microorganisms for the Purposes of Patent Procedure.

*Pseudomonas nitroreducens* DS-S-RP8. International Deposition No. FERM BP-7793. was deposited at the International Patent Organism Depository, National Institute of Advanced Industrial Science and Technology of AIST Tsukuba Central 6, 1-1. Higashi 1-chome. Tsukuba-shi, Ibaraki-ken, 305-8566 Japan. on Jun. 29, 2001, and accepted as established under the Budapest Treaty on the International Recognition of the Deposit of Microorganisms for the Purposes of Patent Procedure.

*Alcaligenes* sp. DS-S-7G. International Deposition No. FERM BP-3098, was deposited at the Fermentation Research Institute. Agency of Industrial Science and Technology, 1-3, Higashi 1-chome, Tsukuba-shi, Ibaraki-ken, 305 Japan, on Nov. 15, 1989, and accepted as established under the Budapest Treaty on the International Recognition of the Deposit of Microorganisms for the Purposes of Patent Procedure.

DETAILED DESCRIPTION OF THE INVENTION

Hereinbelow, the present invention is described in more detail.

The method for obtaining optically active 3-chloro-2-methyl-1,2-propanediol of the present invention comprises a first step of letting at least one kind of microorganism or a processed product thereof that has an ability to leave untouched (R)-3-chloro-2-methyl-1,2-propanediol (CAS No. 118609-22-6) or (S)-3-chloro-2-methyl-1,2-propanediol (CAS No. 120255-23-4) (hereinafter sometimes referred to as "the microorganisms of the invention") in the presence of an enantiomeric mixture of 3-chloro-2-methyl-1,2-propanediol (CAS No. 597-33-1) act on an enantiomeric mixture of 3-chloro-2-methyl-1,2-propanediol; and a second step of recovering the untouched optically active 3-chloro-2-methyl-1,2-propanediol.

Starting Compound

Methods for obtaining an enantiomeric 3-chloro-2-methyl-1,2-propanediol mixture are not limited. For example, it can be obtained by a ring-opening reaction on an enantiomeric 2-methyl-epichlorohydrin mixture. Although any ring-opening reaction can be employed insofar as an enantiomeric 3-chloro-2-methyl-1,2-propanediol mixture is produced, a ring-opening reaction under acidic conditions created by sulfuric acid is preferable.

Microorganisms of the Invention

Microorganisms usable in the present invention are not limited insofar as they have an ability to leave untouched (R)- or (S)-3-chloro-2-methyl-1,2-propanediol in the presence of an enantiomeric 3-chloro-2-methyl-1,2-propanediol mixture.

Microorganisms belonging to the genus *Pseudomonas* are given as examples of microorganisms having an ability to leave untouched (R)-3-chloro-2-methyl-1,2-propanediol. Among such microorganisms, *Pseudomonas* sp. DS-K-436-1 (International Deposition No: FERM BP-7079) and *Pseudomonas* sp. OS-K-29 (International Deposition No: FERM BP-994) are preferable. Microorganisms having an ability to leave untouched (R)-3-chloro-2-methyl-1,2-propanediol can be used singly or as a combination of two or more kinds of them. When a microorganism having an ability to leave untouched (R)-3-chloro-2-methyl-1,2-propanediol is used in the method of the invention, (R)-3-chloro-2-methyl-1,2-propanediol is obtained.

Microorganisms belonging to the genus *Pseudomonas* and microorganisms belonging to the genus *Alcaligenes* are given as examples of microorganisms having an ability to leave untouched (S)-3-chloro-2-methyl-1,2-propanediol. Among such microorganisms, *Pseudomonas* sp. DS-SI-5 (International Deposition No: FERM BP-7080), *Pseudomonas nitroreducens* DS-S-RP8 (International Deposition No: BP-7793), and *Alcaligenes* sp. DS-S-7G (International Deposition No: FERM BP-3098) are preferable. Microorganisms having an ability to leave untouched (S)-3-chloro-2-methyl-1,2-propanediol can be used singly or as a combination of two or more kinds of them. When a microorganism having an ability to leave untouched (S)-3-chloro-2-methyl-1,2-propanediol is used in the method of the invention, (S)-3-chloro-2-methyl-1,2-propanediol is obtained.

Microorganisms of the invention may be in the form of wild strains, mutant strains, genetically recombined strains, strains obtained by cell fusion, etc., insofar as they have an ability to leave untouched one optically active 3-chloro-2-methyl-1,2-propanediol isomer.

The First Step

Microorganisms or processed products thereof are used in the first step. "Processed products" include disrupted microorganisms, enzymes extracted from microorganisms, etc. Microorganisms and processed products thereof may be immobilized according to standard methods.

The term "act on" herein means having a microorganism or a processed product thereof be present together with the substrate, i.e., an enantiomeric 3-chloro-2-methyl-1,2-propanediol mixture, in the same reaction system so as to bring an enzyme and the substrate into contact. The enzyme referred to herein is one present in or around a microorganism or a processed product thereof and that has an ability to stereoselectively decompose a 3-chloro-2-methyl-1,2-propanediol isomer.

In particular, when a microorganism of the invention is used to initiate the reaction, an enantiomeric 3-chloro-2-methyl-1,2-propanediol mixture is introduced into a culture medium in which the microorganism has been cultured.

The composition of the culture medium for culturing the microorganism is not limited insofar as the microorganism can grow. Examples of usable culture media are broths containing a carbon source such as glucose, galactose, sucrose, etc. as a carbohydrate, 1,2-propanediol, 3-chloro-1,2-propanediol, glycerol, etc. as an alcohol, acetic acid, citric acid, malic acid, maleic acid, fumaric acid, gluconic acid, etc. as an organic acid or salt thereof, or a mixture thereof; a nitrogen source such as ammonium sulfate, ammonium nitrate, ammonium phosphate, etc. as an inorganic nitrogen compound, urea, peptone, casein, yeast extract, meat extract, corn steep liquor, etc. as an organic nitrogen source, or a mixture thereof; an inorganic salt such as a phosphate, magnesium salt, potassium salt, manganese salt, iron salt, zinc salt, copper salt or the like; and, as necessary, vitamins. Furthermore, agents that can enhance the generation of optically active 3-chloro-2-methyl-1,2-propanediol, such as 3-chloro-2-methyl-1,2-propanediol and the like can be added to the culture media.

The microorganisms of the invention can be cultured according to standard methods. For example, they can be aerobically cultured for about 10 to about 96 hours in a culture medium with a pH of about 6 to about 9, and preferably about 6.5 to about 7.5, at a temperature of about 20 to about 40° C., and preferably about 25 to about 37° C. Microorganisms obtained by culturing in such a manner are usually in a dormant phase.

Microorganisms in a logarithmic phase or stationary phase are usable. Preferable are those that are highly stereospecific and have strong activities of stereoselective decomposition.

The stereoselective decomposition reaction may be carried out by adding an enantiomeric 3-chloro-2-methyl-1,2-propanediol mixture to a suspension wherein a microorganism recovered from a culture medium has been suspended in a liquid, for example, a buffer.

When an immobilized microorganism, a processed product of a microorganism, or an immobilized processed product of a microorganism is used, the stereoselective decomposition reaction can also be carried out by adding an enantiomeric 3-chloro-2-methyl-1,2-propanediol mixture to a liquid such as a buffer in which such a microorganism product has been suspended or mixed.

In either case, the reaction temperature is preferably about 15 to about 50° C., and particularly preferably about 25 to about 35° C. A sufficient enzymatic activity can be obtained at a temperature within the aforementioned ranges, and thereby the reaction sufficiently proceeds.

The reaction pH is preferably about 4 to about 6.5, and particularly preferably about 5 to about 6. Neutral or acidic conditions are preferable because glycidol is likely to be generated under alkaline conditions due to ring-closure of the substrate. A pH in the aforementioned ranges affords a sufficient enzymatic activity.

The decomposition reaction proceeds more efficiently by bringing the reaction system into aerobic conditions by aeration. The higher the dissolved oxygen concentration in the reaction system, the more preferable. The dissolved oxygen concentration can be increased by, for example, pressuring the reaction system. Although the upper limit of dissolved oxygen concentration cannot be specified, it is usually about 8 ppm under ordinary pressures.

The proportion of the substrate in the reaction mixture is preferably about 0.1 to about 20% (v/v), and preferably about 1 to about 10% (v/v). When the proportion of the substrate is within the aforementioned ranges, an optically active isomer can be efficiently obtained.

The substrate may be introduced into the reaction system in a single batch or in portions. The amount of microorganism or processed product thereof is usually such that the reaction completes in about 1 to about 120 hours.

The reaction is usually carried out while stirring or shaking. Although the reaction time varies depending on the concentration of the substrate, amount of microorganism or processed product thereof, and other factors, the reaction is preferably terminated in about 1 to about 120 hours. The end point of the reaction is preferably determined by measuring the optical purity of the desired optically active isomer by gas chromatographic analysis or the like.

As the reaction progresses, if the pH in the reaction mixture increases or decreases, a suitable alkali or acid may be added to the reaction mixture to control the pH to be within the optimal range. Examples of alkalis are those that are usually used to neutralize acids, such as a calcium carbonate suspension, sodium carbonate solution, potassium carbonate, ammonium carbonate, and like aqueous solutions of alkali salts of carbonic acid; an aqueous sodium hydroxide solution, aqueous potassium hydroxide solution, aqueous calcium hydroxide solution, and like aqueous solutions of hydroxyl alkali salts; an aqueous ammonia solution; etc. Examples of acids are those that are usually used to neutralize alkalis, such as hydrochloric acid, phosphoric acid, etc.

By letting a microorganism or a processed product thereof of the invention act on an enantiomeric 3-chloro-2-methyl-1,2-propanediol mixture, (R)- or (S)-3-chloro-2-methyl-1,2-propanediol is stereoselectively/stereospecifically decomposed.

The Second Step

The resulting optically active 3-chloro-2-methyl-1,2-propanediol that is left in the reaction mixture can be recovered according to standard methods. For example, the microorganism is removed from the reaction mixture by centrifugation, and the supernatant is concentrated by an evaporator and extracted with ethyl acetate, ether or like solvent. Thereafter, the extract is dried using anhydrous magnesium sulfate or the like, and the solvent is removed under reduced pressure, thereby giving an optically active isomer of 3-chloro-2-methyl-1,2-propanediol as a syrup. This propanediol isomer can be purified according to standard techniques such as extraction, distillation, and chromatography.

EXAMPLES

Examples are given below to illustrate the invention in more detail, but the scope of the invention is not limited to these Examples. In the Examples, "%" refers to "% (w/v)" unless otherwise specified.

Example 1

Preparation of 3-chloro-2-methyl-1,2-propanediol

Ion-exchanged water (1700 g) and concentrated sulfuric acid (2.7 g) were introduced into a 3 l flask. The resulting solution was maintained at 65 to 70° C., and 1014.5 g of 2-methyl-epichlorohydrin (manufactured by Daicel Chemical Industries Ltd.) was added dropwise thereto while stirring and then reacted for 5 hours. The 2-methyl-epichlorohydrin and the 3-chloro-2-methyl-1,2-propanediol contained in the reaction solution were quantified by gas chromatography (using a column manufactured by GL Science Co., Ltd., PEG20M, 60-80 mesh (0.31-0.42 mm)). The pH of the reaction solution was adjusted to 6.0 by adding sodium hydrogencarbonate. The reaction solution was then concentrated, thereby giving 1200 g of 3-chloro-2-methyl-1,2-propanediol as a syrup.

Example 2

Reaction Using *Pseudomonas* sp. DS-K-436-1

A culture medium (100 ml, pH 7.0) having a composition of 10 g/l peotone, 10 g/l yeast extract, 10 g/l glycerol was introduced into a 500 ml Erlenmeyer flask equipped with baffles, and autoclaved under pressure at 121° C. for 15 minutes. *Pseudomonas* sp. DS-K-436-1 that had been cultured on a plate medium containing nutrients as described above was inoculated on the sterilized culture medium in a small amount and cultured aerobically at 30° C. for 24 hours. The resulting culture medium was centrifuged to recover the microorganism.

The microorganism was suspended in a 100 ml of 20 mM potassium phosphate buffer (pH 7.0). To the suspension were added racemic 3-chloro-2-methyl-1,2-propanediol prepared as in Example 1 and $CaCO_3$ so as to have final concentrations of 1.0% and 1.5%, respectively, and a reaction was carried out at 30° C. at 120 rpm for 24 hours. The 3-chloro-2-methyl-1,2-propanediol remaining in the reaction mixture was analyzed by gas chromatography (using a column manufactured by GL Science Co., Ltd., PEG20M, 60-80 mesh (0.31-0.42 mm)).

After the reaction, the reaction mixture was subjected to centrifugation to remove the microorganism and to obtain the supernatant fluid. The supernatant fluid was concentrated using an evaporator and extracted with ether. The extract was then dried with anhydrous magnesium sulfate, and ether was removed under reduced pressure, thereby giving 3-chloro-2-methyl-1,2-propanediol as a syrup.

The measurement of the optical purity of this compound was carried out as follows: this 3-chloro-2-methyl-1,2-propanediol was alkali-treated by an aqueous sodium hydroxide solution to convert it into the corresponding optically active 2-methylglycidol; and this optically active 2-methylglycidol was analyzed by gas chromatography using an A-PH capillary column manufactured by Astech Corporation (0.25 mm (ID)×30 m (L)) under following conditions:

Column temperature: 45° C.
Detector temperature: 150° C.
Carrier gas: helium
Initial flow rate: 1.6 ml/min
Linear velocity: 35 cm/sec
Detector: FID
Split ratio: 130/1

The retention time of 2-methylglycidol was 35 minutes for (R)-2-methylglycidol and 31 minutes for (S)-2-methylglycidol. Based on the rotational angle of 3-chloro-2-methyl-1,2-propanediol (Japanese Patent No. 2567430, Example 9 of this application), (R)-2-methylglycidol and (S)-2-methylglycidol were identified, and the retention time thereof was obtained.

3-chloro-2-methyl-1,2-propanediol remained yield of 17.6%. The residual ratio of. This 3-chloro-2-methyl-1,2-propanediol was (R)-3-chloro-2-methyl-1,2-propanediol having an optical purity of at least 99% e.e.

Example 3

Reaction Using *Pseudomonas* sp. OS-K-29

The procedure described in Example 2 was repeated except that *Pseudomonas* sp. DS-K-29 was used as the microorganism. 3-chloro-2-methyl-1,2-propanediol remained in a proportion of 22.1%. This 3-chloro-2-methyl-1,2-propanediol was (R)-3-chloro-2-methyl-1,2-propanediol having an optical purity of at least 99% e.e.

Example 4

Reaction Using *Pseudomonas* sp. DS-SI-5

The procedure of Example 2 was repeated except that *Pseudomonas* sp. DS-SI-5 was used as the microorganism, racemic 3-chloro-2-methyl-1,2-propanediol as produced in Example 1 and $CaCO_3$ were used so as to have final concentrations of 2.5% and 3.6%, respectively, and the reaction time was 48 hours.

3-chloro-2-methyl-1,2-propanediol remained in a proportion of 40.9%. This 3-chloro-2-methyl-1,2-propanediol was (S)-3-chloro-2-methyl-1,2-propanediol having an optical purity of at least 99% e.e.

Example 5

Reaction Using *Pseudomonas nitroreducens* DS-S-RP8

The procedure of Example 2 was repeated except that *Pseudomonas nitroreducens* DS-S-RP8 was used as the microorganism and the reaction time was 48 hours.

3-chloro-2-methyl-1,2-propanediol remained in a proportion of 36.0%. This 3-chloro-2-methyl-1,2-propanediol was (S)-3-chloro-2-methyl-1,2-propanediol having an optical purity of at least 99% e.e.

Example 6

Reaction Using *Alcaligenes* sp. DS-S-7G

The procedure described in Example 1 was repeated except that *Alcaligenes* sp. DS-S-7G was used as the microorganism, the culture medium (pH 7.0) for culturing the microorganism had a composition of 10 g/l peptone, 10 g/l yeast extract, and 10 g/l sodium gluconate, while racemic 3-chloro-2-methyl-1,2-propanediol as produced in Example 2 and $CaCO_3$ were used so as to have final concentrations of 3.0% and 4.2%, respectively.

3-chloro-2-methyl-1,2-propanediol remained in a proportion of 22.4%. This 3-chloro-2-methyl-1,2-propanediol was (S)-3-chloro-2-methyl-1,2-propanediol having an optical purity of at least 99% e.e.

Example 7

Reaction Using *Pseudomonas nitroreducens* DS-S-RP8

| | |
|---|---|
| Sodium gluconate | 2.0% |
| Glycerol | 1.0% |
| Ammonium sulfate | 1.0% |
| Disodium hydrogen phosphate | 0.02% |
| Dipotassium hydrogen phosphate | 0.02% |
| Monosodium dihydrogen phosphate | 0.04% |
| Magnesium sulfate | 0.05% |
| Iron sulfate | 0.001% |
| Copper sulfate | 0.0001% |
| Manganese nitrate | 0.0001% |
| Calcium carbonate | 1.0% |

A culture medium (100 ml, pH 7.0) having the formulation given above was introduced into a 500 ml Erlenmeyer flask equipped with baffles and autoclaved under pressure at 121° C. for 15 minutes. One ml of the *Pseudomonas nitroreducens* DS-S-RP8 culture obtained in the same manner as in Example 2 was aseptically inoculated into the aforementioned culture medium, and the microorganism was cultured aerobically at 30° C. for 24 hours. To the culture medium thus prepared were added 3-chloro-2-methyl-1,2-propanediol as produced in Example 1 and $CaCO_3$ so as to have final concentrations of 2.0% and 3.0%, respectively, and a reaction was carried out at 30° C. at 120 rpm for 72 hours.

The residual ratio and optical purity of the 3-chloro-2-methyl-1,2-propanediol remaining in the reaction mixture were measured as in Example 2. 3-chloro-2-methyl-1,2-propanediol remained in a proportion of 47.0%. This 3-chloro-2-methyl-1,2-propanediol was (S)-3-chloro-2-methyl-1,2-propanediol having an optical purity of at least 99% e.e.

Example 8

Reaction Using *Pseudomonas* sp. DS-SI-5

A culture medium (3.5 l, pH 7.0) having a composition of 10 g/l peptone, 10 g/l yeast extract, and 10 g/l glycerol was autoclaved under pressure at 121° C. for 15 minutes in a 5 l incubator. The *Pseudomonas* sp. DS-SI-5 culture (3.5 ml) obtained in the same manner as in Example 2 was aseptically inoculated into the aforementioned culture medium, and the microorganism was cultured at 30° C. at 450 rpm with a ventilation volume of 0.1 vvm for 24 hours. To the culture medium thus prepared was added 87.5 g of racemic 3-chloro-2-methyl-1,2-propanediol as produced in Example 1 in a final proportion of 2.5%, and a reaction was carried out at 30° C. in 450 rpm in 0.1 vvm for 72 hours. Since the pH tended to decrease as the reaction progressed, 25% NaOH was added dropwise to the reaction system to maintain the pH at 6.0.

After the reaction, the amount of 3-chloro-2-methyl-1,2-propanediol remaining in the reaction mixture and the optical purity thereof were measured as in Example 2. The proportion of 3-chloro-2-methyl-1,2-propanediol after the reaction was 1.1% (residual ratio: 44.0%). This 3-chloro-2-methyl-1,2-propanediol was (S)-3-chloro-2-methyl-1,2-propanediol having an optical purity of at least 99% e.e.

Example 9

Effect of Dissolved Oxygen Concentration

A culture medium (1000 l, pH 7.0) having a composition of 10 g/l peptone, 10 g/l yeast extract, and 10 g/l glycerol was steam-sterilized under pressure at 128° C. for 20 minutes in a 1300 l incubator. The *Pseudomonas* sp. DS-SI-5 culture (500 ml) obtained in the same manner as in Example 2 was aseptically inoculated into the aforementioned culture medium, and the microorganism was cultured at 30° C. at 120 rpm with a ventilation volume of 0.2 vvm for 24 hours. To the culture medium thus prepared was added 25 kg of racemic 3-chloro-2-methyl-1,2-propanediol as produced in Example 1 in a final proportion of 2.5%, and a reaction was carried out at 30° C. at 120 rpm in 0.4 vvm for 72 hours. Since the pH tended to decrease as the reaction progressed, 25% NaOH was added dropwise to the reaction system to maintain the pH at 6.0.

The amount of 3-chloro-2-methyl-1,2-propanediol remaining in the reaction mixture and the optical purity thereof were measured as in Example 2. The proportion of 3-chloro-2-methyl-1,2-propanediol after the reaction was 1.1% (residual ratio: 44.0%). This 3-chloro-2-methyl-1,2-propanediol was (S)-3-chloro-2-methyl-1,2-propanediol having an optical purity of at least 99% e.e ($[\alpha]_D^{20}=+5.92°$, c=3%, $CHCl_3$).

Example 10

Effect of Dissolved Oxygen

The procedure of Example 9 was repeated except that the amount of racemic 3-chloro-2-methyl-1,2-propanediol used in the reaction was 13.7 kg (1.37%), and the ventilation volume during the reaction was 0.1 vvm for the first 6 hours, 0.2 vvm from the $6^{th}$ hour to the $48^{th}$ hour, and 0.4 vvm from the $48^{th}$ hour to the $72^{nd}$ hour. The results showed that when the dissolved oxygen concentration was low due to a small ventilation volume (0.1 to 0.2 vvm), the increase in the optical purity of 3-chloro-2-methyl-1,2-propanediol was small (0 to 36 hours of reaction). When the ventilation volume was increased (to 0.4 vvm), the dissolved oxygen concentration increased, and the increase in the optical purity of 3-chloro-2-methyl-1,2-propanediol was significant (during the $36^{th}$ to $72^{nd}$ hours of reaction).

With respect to Examples 9 and 10, Table 1 below shows the correlation between dissolved oxygen concentration and optical purity during the reaction. It can be understood that when the dissolved oxygen concentration is increased, the optical purity is significantly enhanced.

TABLE 1

| | Example 9 | | | Example 10 | | |
|---|---|---|---|---|---|---|
| Reaction time | Ventilation volume (vvm) | Dissolved oxygen concentration (ppm) | Optical purity (% e.e.) | Ventilation volume (vvm) | Dissolved oxygen concentration (ppm) | Optical purity (% e.e.) |
| 0 | 0.4 | 0 | | 0.1 | 0 | |
| 3 | 0.4 | 0.6 | | 0.1 | 0 | |
| 6 | 0.4 | 2.7 | | 0.2 | 0 | |
| 12 | 0.4 | 3.9 | | 0.2 | 0 | 0 |
| 18 | 0.4 | 4.5 | | 0.2 | 0 | |
| 24 | 0.4 | 5.0 | 77.9 | 0.2 | 0 | 7.6 |
| 30 | 0.4 | 5.3 | | 0.2 | 0 | |
| 36 | 0.4 | 5.5 | 90.1 | 0.2 | 0 | 20.3 |
| 42 | 0.4 | 5.5 | | 0.2 | 0.4 | |
| 48 | 0.4 | 5.4 | 94.5 | 0.4 | 1.5 | |
| 54 | 0.4 | 5.3 | | 0.4 | 4.4 | |
| 60 | 0.4 | 5.2 | | 0.4 | 4.8 | |
| 66 | 0.4 | 5.3 | 99.0 | 0.4 | 5.0 | 85.3 |
| 72 | 0.4 | 5.2 | | 0.4 | 5.0 | 93.5 |

As described above, through reactions taking advantage of the microorganisms of the present invention, optically active 3-chloro-2-methyl-1,2-propanediol of high optical purity, i.e., 99% e.e. or greater, can be readily produced in large amounts.

We claim:

1. A method for obtaining optically active 3-chloro-2-methyl-1,2-propanediol, the method comprising:
   a first step of letting at least one kind of microorganism or processed product thereof having an ability to leave untouched (R)-3-chloro-2-methyl-1,2-propanediol or (S)-3-chloro-2-methyl-1,2-propanediol in the presence of an enantiomeric 3-chloro-2-methyl-1,2-propanediol mixture act on an enantiomeric 3-chloro-2-methyl-1,2-propanediol mixture; and
   a second step of recovering the untouched optically active 3-chloro-2-methyl-1,2-propanediol.

2. The method according to claim 1, wherein the microorganism is at least one kind of microorganism belonging to the genus *Pseudomonas* and having an ability to leave untouched (R)-3-chloro-2-methyl-1,2-propanediol in the presence of an enantiomeric 3-chloro-2-methyl-1,2-propanediol mixture, and the optically active 3-chloro-2-methyl-1,2-propanediol obtained is (R)-3-chloro-2-methyl-1,2-propanediol.

3. The method according to claim 2, wherein the microorganism belonging to the genus *Pseudomonas* is at least one kind of microorganism selected from the group consisting of *Pseudomonas* sp. DS-K-436-1 (International Deposition No: FERM BP-7079) and *Pseudomonas* sp. OS-K-29 (International Deposition No: FERM BP-994).

4. The method according to claim 1, wherein the microorganism is at least one kind of microorganism that is selected from the group consisting of microorganisms belonging to the genus *Pseudomonas* and microorganisms belonging to the genus *Alcaligenes* and that has an ability to leave untouched (S)-3-chloro-2-methyl-1,2-propanediol in the presence of an enantiomeric 3-chloro-2-methyl-1,2-propanediol mixture, and the optically active 3-chloro-2-methyl-1,2-propanediol obtained is (S)-3-chloro-2-methyl-1,2-propanediol.

5. The method according to claim 4, wherein the microorganism is at least one kind of microorganism selected from the group consisting of *Pseudomonas* sp. DS-SI-5 (International Deposition No: FERM BP-7080), *Pseudomonas nitroreducens* DS-S-RP8 (International Deposition No: BP-7793), and *Alcaligenes* sp. DS-S-7G (International Deposition No: FERM BP-3098).

6. The method according to claim 1, wherein the first step is carried out under aerobic conditions.

7. The method according to claim 1, wherein in the first step, the pH of the reaction system is 4 to 6.5.

8. The method according to claim 1, wherein the enantiomeric 3-chloro-2-methyl-1,2-propanediol mixture is obtained by ring-opening hydrolyzing an enantiomeric 2-methyl-epichlorohydrin mixture under acidic conditions created by sulfuric acid.

9. A method for obtaining optically active 3-chloro-2-methyl-1,2-propanediol, comprising:
   providing a culture medium in which at least a microorganism or processed product thereof having an ability to leave untouched (R)-3-chloro-2-methyl-1,2-propanediol or (S)-3-chloro-2-methyl-1,2-propanediol is cultured, wherein an enzyme having an ability to stereoselectively decompose a 3-chloro-2-methyl-1,2-propanediol isomer is present in or around the microorganism or processed product thereof;
   introducing an enantiomeric 3-chloro-2-methyl-1,2-propanediol mixture as a substrate into the culture medium to contact the enzyme and the enantiomeric 3-chloro-2-methyl-1,2-propanediol mixture, thereby stereoselectively decomposing a 3-chloro-2-methyl-1,2-propanediol isomer in the enantiomeric 3-chloro-2-methyl-1,2-propanediol mixture; and
   recovering untouched optically active 3-chloro-2-methyl-1,2-propanediol present in the enantiomeric 3-chloro-2-methyl-1,2-propanediol mixture.

10. The method according to claim 9, wherein the microorganism is selected from the group consisting of *Pseudomonas* sp. DS-K-436-1 (International Deposition No: FERM BP-7079), *Pseudomonas* sp. OS-K-29 (International Deposition No: FERM BP-994), *Pseudomonas* sp. DS-SI-5 (International Deposition No: FERM BP-7080), *Pseudomonas nitroreducens* DS-SRP8 (International Deposition No: BP-7793), and *Alcaligenes* sp. DS-S-7G (International Deposition No: FERM BP-3098).

11. The method according to claim 9, wherein the decomposition reaction is carried out under aerobic conditions by aeration.

12. The method according to claim 9, wherein the decomposition reaction is carried out at a pH of 4 to 6.5.

13. The method according to claim 9, wherein the substrate is introduced in a concentration of about 0.1% (v/v) to about 20% (v/v).

14. The method according to claim 9, further comprising ring-opening hydrolyzing an enantiomeric 2-methyl-epichlorohydrin mixture under acidic conditions created by sulfuric acid to obtain the enantiomeric 3-chloro-2-methyl-1,2-propanediol mixture.

* * * * *